US005482698A

United States Patent [19]

Griffiths

[11] Patent Number: 5,482,698

[45] Date of Patent: Jan. 9, 1996

[54] DETECTION AND THERAPY OF LESIONS WITH BIOTIN/AVIDIN POLYMER CONJUGATES

[75] Inventor: Gary L. Griffiths, Morristown, N.J.

[73] Assignee: Immunomedics, Inc., Morris Plains, N.J.

[21] Appl. No.: 51,144

[22] Filed: Apr. 22, 1993

[51] Int. Cl.[6] .......................... A61K 41/00; A61K 51/10; A61K 31/74; A61K 31/415

[52] U.S. Cl. ........................ 424/141; 424/1.45; 424/1.49; 424/1.69; 424/9.34; 424/9.35; 424/9.36; 424/9.4; 424/9.6; 424/78.08; 514/387

[58] Field of Search ................................ 424/1.49, 1.41, 424/1.45, 1.69, 9, 85.91, 78.08, 9.34, 9.35, 9.36, 9.4, 9.6; 514/2, 12, 387

[56] References Cited

U.S. PATENT DOCUMENTS

| | | | |
|---|---|---|---|
| 4,782,840 | 11/1988 | Martin, Jr. et al. | 128/654 |
| 4,863,713 | 9/1989 | Goodwin et al. | 424/1.1 |
| 4,932,412 | 6/1990 | Goldenberg | 128/654 |
| 4,948,590 | 8/1990 | Hawrot et al. | 424/450 |
| 4,952,685 | 8/1990 | Stavrianopoulos | 536/27 |
| 5,026,785 | 6/1991 | Mage et al. | 525/329 |
| 5,057,313 | 10/1991 | Shih et al. | 424/85.91 |
| 5,082,830 | 1/1992 | Brakel et al. | 514/44 |
| 5,155,215 | 10/1992 | Ranney | 534/16 |
| 5,169,933 | 12/1992 | Anderson et al. | 530/391.3 |
| 5,196,351 | 3/1993 | Harris et al. | 436/501 |
| 5,283,342 | 2/1994 | Gustavson et al. | 548/304.1 |
| 5,326,778 | 7/1994 | Rosebrough | 514/387 |
| 5,364,614 | 11/1994 | Platzek et al. | 424/9 |
| 5,420,105 | 5/1995 | Gustavson et al. | 514/2 |

FOREIGN PATENT DOCUMENTS

| | | |
|---|---|---|
| 0496074A1 | 7/1992 | European Pat. Off. . |
| WO93/25240 | 12/1993 | WIPO . |

OTHER PUBLICATIONS

Paganelli et al., "In Vivo Labelling Of Biotinylated Monoclonal Antibodies By Radioactive Avidin: A Strategy To Increase Tumor Radiolocalization", Int. J. Cancer: Supplement, vol. 2:121–125, (1988).

Schechter et al., "Indirect Immunotargeting Of Cis–Pt To Human Epidermoid Carcinoma KB Using The Avidin Biotin System", Int. J. Cancer, vol. 48:167–172, (1991).

Hnatowich et al., "Investigations Of Avidin And Biotin For Imaging Applications", The Journal Of Nuclear Medicine, vol. 28:1294–1302, (1987).

Klibanov et al., "Blood Clearance Of Radiolabeled Antibody: Enhancement By Lactosamination And Treatment With Biotin–Avidin Or Anti–Mouse IgG Antibodies", J. Nucl. Med., vol. 29:1951–1956, (1988).

Paganelli et al., "Three–Step Monoclonal Antibody Tumor Targeting In Carcinoembryonic Antigen–Positive Patients", Cancer Research, vol. 51:5960–5966, (1991).

Stickney et al., "Bifunctional Antobody: A Binary Radiopharmaceutical Delivery System For Imaging Colorectal Carcinoma", Cancer Research, vol. 51:6650–6655, (1991).

Yuan et al., "Pharmacokinetic Analysis Of Two–Step Approaches Using Bifunctional And Enzyme–Conjugated Antibodies", Cancer Research, vol. 51:3119–3130, (1991).

Paganelli et al., "Tumor Targeting In Patients With Ovarian Cancer Using Biotinylated Monoclonal Antibodies And Radioactive Streptavidin", Proceedings of the 37th Annual Meeting, vol. 31:735, (1990).

Green et al., "The Use Of Bifunctional Biotinyl Compounds To Determine The Arrangement Of Subunits In Avidin", Biochem. J., vol. 125:781–791, (1971).

Sinitsyn et al., "Rapid Blood Clearance Of Biotinylated IgG After Infusion Of Avidin", J. Nucl. Med. vol. 30:66–69, (1989).

Paganelli et al., "Monoclonal Antibody Pretargeting Techniques For Tumor Localization: The Avidin–Boitin System", Nuclear Medicine Communications, vol. 12:211–234, (1991).

Oehr et al., "Streptavidin And Biotin As Potential Tumor Imaging Agents", The Journal Of Nuclear Medicine, vol. 29:728–729, (1988).

Kalofonos et al., "Imaging Of Tumor In Patients With Indium–111–Labeled Biotin And Streptavidin–Conjugated Antibodies: Preliminary Communication", Journal Of Nuclear Medicine, vol. 31:1791–1796, (1990).

Goodwin et al., "Pre–Targeted Immunoscintigraphy Of Murine Tumors With Indium–111–Labeled Bifunctional Haptens", J. Nucl. Med., vol. 29:226–234, (1988).

Torchilin et al., 11, 1989, pp. 297–303.

*Primary Examiner*—Shean Wu
*Assistant Examiner*—Lara E. Chapman
*Attorney, Agent, or Firm*—Foley & Lardner

[57] ABSTRACT

Methods of detecting and/or treating lesions in a patient are provided. The methods are an improvement over known methods comprising the steps of (a) parenterally injecting a subject with a targeting composition comprised of a biotin-protein conjugate or an avidin-protein conjugate, wherein the protein preferentially binds to a marker substance produced or associated with the targeted lesion, and allowing the protein conjugate to preferentially accrete at the targeted lesion; (b) then parenterally injecting a clearing composition comprised of (i) avidin, when the targeting composition is a biotin-protein conjugate, or (ii) biotin, when the targeting composition is a avidin-protein conjugate, and allowing the clearing composition to substantially clear the targeting composition from non-targeted sites and to bind to the targeting composition accreted at the targeted lesion; and (c) parenterally injecting a detection or therapeutic composition comprised of a conjugate of (i) avidin and detection or therapeutic agent when the clearing composition is biotin, or (ii) biotin and detection or therapeutic agent when the clearing agent is avidin, and allowing the composition to accrete at the targeted lesion. The improvement is having at least one of the compositions of step (a) or (b) further comprise a polymer to which multiple moieties of avidin or biotin can conjugate, thereby providing an increased number of binding sites to which a subsequently administrated composition can bind thereby amplifying the amount of detection or therapeutic agent at the targeted site.

43 Claims, No Drawings

DETECTION AND THERAPY OF LESIONS WITH BIOTIN/AVIDIN POLYMER CONJUGATES

BACKGROUND OF THE INVENTION

1. Field of the Invention

The present invention relates to improved methods for detecting and treating pathological conditions with a multi-step process using compositions containing biotin and/or avidin conjugates.

2. Description of the Prior Art

Antibodies against different determinants associated with pathological and normal cells, as well as associated with pathogenic microorganisms, have been used for the detection and treatment of a wide variety of pathological conditions or lesions. The targeting antibody is conjugated to an appropriate detecting or therapeutic agent as described, for example, in Hansen et al., U.S. Pat. No. 3,927,193 and Goldenberg, U.S. Pat. Nos. 4,331,647, 4,348,376, 4,361, 544. 4,468,457, 4,444,744, 4,460,459, 4,460,561, 4,624,846 and 4,818,709, the disclosure of all of which are incorporated herein by reference.

When detecting a lesion a high signal-to-background ratio needs to be achieved. Therapy also requires a high absolute accretion of the therapeutic agent in the lesion, as well as a reasonably long duration of uptake and binding. High background levels of non-targeting antibody have long been recognized as a major impediment to high target:background ratios being achieved. To overcome this impediment various methods have been developed, such as those described in the above-referenced Goldenberg patents.

Still other methods have been developed to increase the target:background ratios of the detection or therapeutic agents, such as pre-targeting and biotin/avidin approaches, as described, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; Stickney et al., Cancer Res. 51:6650, 1991; and Yuan et al., Cancer Res. 51:3119, 1991; all incorporated herein in their entirety by reference.

Avidin, found in egg whites, has a very high binding affinity for biotin, which is a B-complex vitamin (Wilcheck et al., Anal. Biochem, 171:1, 1988). Streptavidin, derived from Streptomyces avidinii, is similar to avidin, but has lower non-specific tissue binding, and therefore often is used in place of avidin. Both avidin and streptavidin have a tetravalency for biotin, thus permitting amplification when the former bind to biotin.

In a prior art 2-step procedure, a targeting antibody is conjugated with either avidin or biotin and then is injected into a patient, thus localizing the avidin or biotin at a tumor of interest. Thereafter, either biotin or avidin (depending on which was coupled to the targeting antibody), bearing an imaging isotope is injected and is localized at the site of the primary antibody by binding to avidin or biotin respectively.

Timing of the second injection after the first one is very critical. Injecting the radiolabeled avidin or biotin too early will increase the avidin/biotin conjugates in the bloodstream and nontargeted tissues, while injecting very late may decrease the amount targeted to the tumor because of reduced retention of the primary antibody at the tumor.

Paganelli et al. (Int. J. Cancer 2:121, 1988) and Kalofonos et al. (J. Nucl. Med. 31:1791, 1990) demonstrated the feasibility of the above approach (the former used biotinylated antibody; the latter used streptavidin-conjugated antibody for tumor localization). In work reported by Kalofonos et al. (ibid.), 3 of 10 patients showed improved imaging. However, the patients also showed that labeled biotin alone (without antibody pretargeting) could detect tumors in 8 of 10 patients.

Paganelli et al. (J. Nucl. Med. 31:735, 1990 and Cancer Res. 51:5960, 1991) disclose a 3-step approach wherein a biotinylated antibody is administered, followed by cold, i.e., non-labeled and non-conjugated, avidin to clear nontargeted antibody, and then a radiolabeled biotin is given which binds to the avidin retained in the body, presumably where the avidin has complexed to the biotinylated antibody. By this method, Paganelli et al. were able to show, with the exception of the kidneys, high tumor:normal organ ratios. Paganelli, et al. (Cancer Res. 51:5960, 1991) used biotinylated DTPA (diethylene triamine pentacetic acid) obtained commercially, which is DTPA linked through two of its carboxylate functions to two biotin residues. The use of biotinylated DTPA has two adverse effects. First, the ability of DTPA to strongly bind therapeutic nuclides in vivo is considerably compromised when two of its five carboxyl groups are substituted. Second, since avidin stereochemistry as taught by Green et. al. (Biochem. J. 125:781, 1971) has shown that four biotin binding sites are located, two each, on opposite faces of the macromolecule, the two same-face binding sites can be bridged by bis biotinylated compounds of suitable chain length. The bis biotinylated DTPA used by Paganelli is long enough in chain length (22 Å) and flexible enough to bridge the distance between the two binding sites (15 Å); thereby, one molecule of this agent will bind to two binding sites on the avidin and reduce the amount of localization possible.

Therefore, a need exists for better methods and compositions which will allow for the higher and more selective targeting and retaining of detection and therapeutic agents to and at pathological lesions.

OBJECTS OF THE INVENTION

The principal object of the present invention is to provide a method to deliver higher absolute amounts and higher target:nontarget ratios of detection or therapeutic agents.

Another object of the invention is to provide a multiple-step procedure which targets higher amounts of a detection or therapeutic agent to a lesion.

Upon further study of the specification and appended claims, further objects and advantages of this invention will become apparent to those skilled in the art.

SUMMARY OF THE INVENTION

This invention relates to improved methods of detecting and/or treating lesions in a patient. The methods are an improvement over known methods comprising the steps of (a) parenterally injecting a subject with a targeting composition comprised of a biotin-protein conjugate or an avidin-protein conjugate, wherein the protein preferentially binds to a marker substance produced or associated with the targeted lesion, and allowing the protein conjugate to preferentially accrete at the targeted lesion; (b) then parenterally injecting a clearing composition comprised of (i) avidin, when the targeting composition is a biotin-protein conjugate, or (ii) biotin, when the targeting composition is a avidin-protein conjugate, and allowing the clearing composition to substantially clear the targeting composition from non-targeted sites and to bind to the targeting composition accreted at the targeted lesion; and (c) parenterally injecting a detection or therapeutic composition comprised of a conjugate of (i) avidin and detection or therapeutic agent when the clearing composition is biotin, or (ii) biotin and detection or therapeutic agent when the clearing agent is avidin, and allowing the composition to accrete at the targeted lesion. The improvement is having at least one of the compositions of step (a) or (b) further comprise a polymer to which multiple moieties of avidin or biotin can conjugate, thereby providing an increased number of binding sites to which a subsequently administrated composition can bind thereby amplifying the amount of detection or therapeutic agent at the targeted site.

In one embodiment, the method provides a method of detecting and/or treating lesions in a patient. The method comprises the steps of (a) injecting a subject with a first composition comprised of
  (1) multibiotin-polymer-protein conjugate, or
  (2) biotin-protein conjugate, wherein the protein binds to a marker substance produced by or associated with the target lesion, and allowing the biotin-polymer-protein conjugate to accumulate at the target lesion to provide biotin receptors;

(b) injecting a clearing agent comprised of
  (1) avidin,
  (2) multiavidin-polymer conjugate,
  (3) multiavidin-multitherapeutic/detection agent-polymer conjugate,
  (4) avidin-therapeutic/detection agent conjugate, or
  (5) multiavidin-therapeutic/detection agent-polymer conjugate, and permitting the clearing agent to remove circulating biotin-polymer-protein conjugate;

(c) injecting a localizing agent comprised of
  (1) avidin,
  (2) multiavidin-polymer conjugate,
  (3) multiavidin-multitherapeutic/detection agent-polymer conjugate,
  (4) avidin-therapeutic/detection agent conjugate, or
  (5) multiavidin-therapeutic/detection agent-polymer conjugate, wherein the localizing agent may be the same as or different from the clearing agent and can be injected concurrently with or subsequent to the clearing agent, and permitting the localizing agent to localize at the target lesion by binding to a biotin receptor;

(d) injecting a composition comprising
  (1) biotin/detection or therapeutic agent conjugate,
  (2) polymer-multibiotin conjugate or,
  (3) polymer-multibiotin—multi-therapeutic/detection agent conjugate and permitting a biotin of the composition of (d) to bind to an avidin receptor of the localized agent of (c);

(e) if a conjugate containing polymer is used in (d), then injecting a composition comprising
  (1) avidin-therapeutic/detection agent conjugate,
  (2) multiavidin-polymer conjugate,
  (3) avidin, or
  (4) multiavidin-multitherapeutic/detection agent-polymer conjugate, and permitting an avidin of the composition of (e) to bind to a biotin receptor of localized composition of (d);

(f) if other then the avidin-therapeutic/detection agent conjugate has been injected in step (e), injecting a biotin-therapeutic/detection agent conjugate and permitting the biotin to bind to an avidin receptor at the target lesion; and (g) using the therapeutic/detection agent to treat or detect the targeted lesion; wherein a polymer conjugate is used in at least one step of the process and the polymer has a sufficiently rigid stereochemical structure so that only one avidin or biotin of the conjugate will bind to a receptor already present at the target lesion. Most favorably, in the foregoing, the avidin bound therapeutic/detection agents of the clearing and localizing compositions which do not bind to the target lesion, will be readily metabolized and excreted, primarily by the liver and kidney.

In another embodiment, the method provides a method of detecting and/or treating lesions in a patient. The method comprises the steps of (a) injecting a subject with a first composition comprised of a multiavidin-polymer-protein conjugate or avidin-protein conjugate, wherein the protein binds to a marker substance produced by or associated with the target lesion, and allowing the conjugate to accrete at the target lesion;

(b) injecting a clearing agent comprised of
  (1) biotin,
  (2) multibiotin-polymer conjugate,
  (3) multibiotin-multitherapeutic/detection agent-polymer conjugate, or
  (4) biotin-therapeutic/detection agent conjugate, and permitting the clearing agent to remove circulating multiavidin-polymer-protein conjugate of the first composition;

(c) injecting a localizing agent comprised of
  (1) multibiotin-polymer conjugate,
  (2) multibiotin-multitherapeutic/detection agent-polymer conjugate, or
  (3) biotin-therapeutic/detection agent conjugate, wherein the localizing agent may be the same as or different from the clearing agent and can be injected concurrently with or subsequent to the clearing agent and permitting the localizing agent to localize at the target lesion by binding to an avidin receptor;

(d) injecting a composition comprised of
  (1) avidin-detection/therapeutic agent conjugate,
  (2) polymer-multiavidin conjugate or,
  (3) polymer-multiavidin-multitherapeutic/detection agent conjugate, and permitting avidin of the conjugate to bind to biotin receptors of the localizing agent;

(e) if a conjugate containing polymer is used in (d), then injecting a composition consisting essentially of
  (1) biotin-therapeutic/detection agent conjugate,
  (2) multibiotin-polymer conjugate,
  (3) multibiotin-multitherapeutic/detection agent-polymer conjugate, and permitting the biotin of the conjugate to bind to avidin receptors provided by composition (d);

(f) if other than a biotin-therapeutic/detection agent has been injected in step (e), injecting an avidin-therapeutic/detection agent conjugate and permitting the avidin of the conjugate to bind to a biotin receptor at the target lesion; and (g) using the detection/therapeutic agent to detect or treat the targeted lesion; wherein a polymer conjugate is used in at least one step of the method and the polymer has a sufficiently rigid stereochemical structure so that only one biotin or avidin of each conjugate can bind to a receptor already present at the target lesion. Most favorably, in the foregoing, the biotin bound therapeutic/detection agents of the clearing and localizing compositions which do not bind to a receptor at the target lesion will be readily metabolized and excreted, primarily by the liver and/or liver.

In another embodiment, the invention provides a method of detecting and/or treating lesions in a patient. The method comprises (a) injecting a subject with a first composition comprised of a multibiotin-polymer-protein conjugate, wherein the protein preferentially binds to a marker substance produced or associated with the target lesion, and allowing the multibiotin-polymer-protein conjugate to preferentially accrete at the targeted lesion and to provide multiple biotin receptors at the targeted lesion;

(b) injecting at least one dose of a composition comprised of avidin and permitting it to clear the multibiotin-polymer-protein conjugate from non-targeted sites and to localize at the targeted lesion by binding to the multiple biotin receptors;

(c) injecting a composition comprising a biotin-detection agent conjugate or biotin-therapeutic agent conjugate and permitting the biotin to bind to the multiple avidin receptors at the targeted lesion; and (d) using the detection or therapeutic agent to detect or treat the targeted lesion.

In another embodiment, the invention provides another method of treating and/or detecting lesions in a patient. The method comprises (a) injecting a subject with a first composition comprised of a biotin-protein conjugate, wherein the protein preferentially binds to a marker substance produced or associated with the target lesion, and allowing the biotin-protein conjugate to accrete at the target lesion thereby providing biotin receptors at the target lesion;

(b) injecting at least one dose of a clearing and localizing composition comprised of a polymer conjugated to more than one avidin molecule and permitting the conjugate to clear the biotin-protein conjugate from non-targeted sites and to bind to the biotin-protein conjugate accreted at the target lesion, wherein only one avidin of each multiavidin-polymer conjugate binds to a biotin receptor at the target lesion and thereby provides increased numbers of avidin receptors at the target lesion;

(c) injecting a biotin-therapeutic/detection agent conjugate and permitting the biotin of the conjugate to bind to avidin receptors at the target site and thereby increasing the amount of biotin-therapeutic/detection agent accreted at the target lesion; and (d) using the therapeutic/detection agent to treat or detect the lesion.

In another embodiment, the invention provides another method of detecting and treating lesions in a patient. The method comprises the steps of (a) injecting a subject with a first composition comprised of a biotin-protein conjugate, wherein the protein preferentially binds to a marker substance produced by or associated with the target lesion, and allowing the biotin-protein conjugate to bind to the target lesion thereby producing biotin receptors at the target lesion;

(b) injecting at least one dose of a clearing and localizing composition comprised of multiavidin-polymer-detection/therapeutic agent conjugate and permitting the conjugate to clear biotin-protein from non-targeted sites and to localize at the target lesion, wherein only one avidin of each conjugate binds to a biotin receptor present at the target lesion, thereby providing the target lesion with detection or therapeutic agent and an amplified number of avidin binding sites; wherein cleared biotin-protein and non-accreting multiavidin/polymer/detection or therapeutic agent conjugate are metabolized and excreted from the body;

(c) injecting a biotin-detection/therapeutic agent conjugate and permitting the conjugate to preferentially bind in an amplified manner to the multi-avidin sites provided by the conjugate of step (b) at the target lesion; and (d) using the detection/therapeutic agent to detect or treat the target lesion.

In another embodiment, the invention provides another method of treating and detecting lesions in a patient. The method comprises (a) injecting a subject with a first composition comprised of an avidin-protein conjugate, wherein the protein preferentially binds to a marker substance produced or associated with the target lesion and allowing the avidin/protein conjugate to accrete at the target lesion thereby providing avidin receptors at the target lesion;

(b) injecting at least one dose of a clearing and localization agent comprised of a multibiotin-polymer conjugate and allowing the agent to clear the avidin-protein conjugate from non-targeted sites and to localize at the target lesion, wherein only one biotin of each multibiotin-polymer conjugate binds to an avidin receptor provided by each avidin/polymer conjugate accreted at the target lesion, whereby each multibiotin-polymer conjugate provides multiple biotin receptors at the target lesion;

(c) injecting an avidin-therapeutic/detection agent conjugate and allowing the conjugate to bind to the biotin receptors at the target lesion, thereby amplifying the amount of therapeutic/detection agent available at the target lesion; and (d) using the amplified amount of therapeutic/detection agent accreted at the target lesion to detect or treat the target lesion.

In another embodiment, the invention provides another method of detecting and treating lesions in a patient. The method comprises the steps of (a) injecting a subject with a first composition comprised of an avidin-protein conjugate, wherein the protein preferentially binds to a marker substance produced by or associated with the target lesion, and allowing the avidin-protein conjugate to preferentially bind to the targeted lesion and provide avidin receptors;

(b) injecting at least one dose of a clearing and localizing composition comprised of multibiotin-polymer-detection/therapeutic agent conjugate and permitting the conjugate to clear avidin-protein conjugate from non-target sites and to localize at the target lesion, wherein only one biotin of each multibiotin-polymer conjugate binds to an avidin receptor provided by each avidin/polymer conjugate accreted at the target lesion, whereby each multibiotin-polymer-detection/therapeutic agent conjugate provides multiple biotin receptors and provides detection/therapeutic agent to the target lesion; wherein cleared biotin-protein and non-accreting multibiotin-polymer-detection/therapeutic agent conjugate are metabolized and excreted from the body;

(c) injecting an avidin-detection/therapeutic agent conjugate and permitting the conjugate to bind in an amplified manner to the multi-biotin receptors at the target tissue; and (d) using the amplified amount of detection/therapeutic agent at the target lesion to detect or treat the lesion.

DETAILED DISCUSSION

It has now been found that the procedures of the present invention are more advantageous for selective detection and therapy of lesions than the methods of the prior art because of the significant increase in the amount of the detection or therapeutic agent which is available at the targeted site due to the increase in the number of biotin and/or avidin binding sites available at the targeted site.

In a more preferred embodiment of this invention involving a 3-step approach, a multibiotin-polymer-targeting antibody or fragment is injected, followed by the application of avidin as a clearing and localizing agent. Then, as a third step, a biotin-conjugated isotope or drug is administered.

In another preferred 3-step method of the present invention, the first step is the injection of a multibiotin-polymer-antibody or fragment and the second step is the injection of a multiavidin/polymer clearing and localizing agent or chase. The third step involves the injection of biotin conjugated with a detection or therapeutic agent.

Each of these approaches is an improvement, in terms of absolute amount of detection or therapeutic agent delivered and retained at the site of the lesion, as compared to the prior art procedures which do not contemplate the use of a polymer to provide multiple biotin or avidin sites to which a later injected avidin or biotin containing conjugate could bind, thereby amplifying the amount of detection or therapeutic agents available at the targeted site.

Of course, if desired, the sequence can be repeated for additional accumulation of the agents, if desired. Further, the lesion-localizing protein can be a bispecific or hybrid antibody, whereby at least 2 antibody arms are directed against different epitopes of the same antigen or against different substances associated with the lesion. This is preferred in order to achieve higher levels of accretion and binding in the lesion.

These methods of the present invention provide the following improved results over other sequences reported earlier by others:

1. increased absolute amounts of detection and therapeutic agents targeted to the lesion;
2. higher lesion:normal organ (including kidney) ratios; and thereby
3. improved lesion detection or therapy.

The detection/therapeutic agents used in the methods of the present invention can be any or multiples of the following:

A—diagnostic or therapeutic agents (e.g.,alpha-, beta-, gamma-, positron-, x-ray- and fluorescence-emitters; electron- and neutron-capturing agents);

B—photoactivated dyes for detection or therapy;

C—cytotoxic agents (e.g., drugs, toxins, hormones, cytokines, hormone antagonists, receptor antagonists);

D—differentiation agents (e.g., vitamins, cytokines, autocrines, certain hormones and drugs).

The methods of the present invention can be used to detect (either by internal procedures or by external imaging) and/or treat lesions, including cancers, infectious diseases, cardiovascular diseases and other pathological conditions.

Internal detection procedures include intraoperative, intravascular or endoscopic, including laparoscopic, techniques, both surgically invasive and noninvasive.

The polymers most useful in the present invention are those which have a restricted stereochemistry. Such polymers allow for the adequate spacing of biotin (or avidin) moieties such that each biotin (or avidin) is capable of binding to an avidin (or biotin) moiety when its complimentary species is subsequently injected. Also, if the polymer conjugate is the subsequently injected composition and multiple biotin or avidin moieties are conjugated to the polymer, the position of the biotin or avidin residue and the relative rigidity of the polymer due to the restricted stereochemistry will be sufficient such that substantially only one of the multiple residue sites of the conjugate will be able to bind to a complimentary receptor site already present at the targeted lesion as a result of a previously injected composition. For example, biotin units substituted onto the polymer backbone will be unable to bind two avidin receptors present at the target lesion because (1) each biotin of the polymer conjugate will be more than 15 Å from its neighbor and (2) the polymer will be sufficiently sterically rigid to not bend to enable two or more biotin units to bind with the corresponding number of avidin receptors. In this way, the fullest possible targeting amplification is achievable.

Such polymers can be selected by one skilled in the art from the well-known group of commercially available agents such as polyamino-acids, proteins, oligodeoxyribonucleotides, oligonucleotides, polyimines, polysaccharides, polyamines, polycarboxylic acids or polyalcohols. Preferred are polymers having a molecular weight of 5 to 200 kD, most preferably 20 to 60 kD.

More preferred polymers are exemplified by a starburst dendrimer or a dextran, suitably modified for substitution, most preferably to carry a limited number of amino groups.

Dextran is structured in a rigid straight chain. A starburst dendrimer is a sphere having amino units on its outer surface where substitutions can be made.

Commercial biotins products are available in which the biotin has been modified by the addition of alkyl groups. The biotins preferred for use in the present invention are biotin itself or modified biotins having shorter alkyl (C1- 5) chains. The use of a longer chain alkyl modified biotin would allow the biotin to bind an avidin which already has one of its four receptors bound by a neighboring biotin.

Other useful biotin derivatives include active esters, amines, hydrazides and thiol groups with the complimentary reactive groups on polymers being amines, acyl and alkyl leaving groups, carbonyl groups and alkyl halides or Michael-type acceptors.

Avidins are a family of proteins functionally defined by their ability to bind biotin with high affinity and specificity.

Avidins are fairly small oligomeric proteins, made up of four identical subunits, each bearing a single binding site for biotin. Avidins can therefore bind up to four moles of biotin per mole of avidin.

Avidins include proteins (a) produced by amphibians, reptiles and avians, which is present in their eggs and known as avidin, and (b) produced by a streptomyces, *Streptomyces avidinii,* and known as streptavidin. As used herein "avidin" includes all of the above proteins.

Since each avidin moiety has four receptors for biotin, the conjugates containing avidin do not need to have multiple moieties of avidin in order for the amplification resulting from the methods of the present invention to occur. It is preferable, however that multiavidin conjugates be utilized in the methods of the invention.

Proteins are known which preferentially bind marker substances that are produced by or associated with lesions. For example, antibodies can be used against cancer-associated substances, as well as against any pathological lesion that shows an increased or unique antigenic marker, such as against substances associated with cardiovascular lesions, for example, vascular clots including thrombi and emboli, myocardial infarctions and other organ infarcts, and atherosclerotic plaques; inflammatory lesions; and infectious and parasitic agents. Examples of appropriate applications are provided in the above-referenced and incorporated Goldenberg patents and applications.

The cancer states include carcinomas, melanomas, sarcomas, neuroblastomas, leukemias, lymphomas, gliomas, myelomas and neural tumors.

The infectious diseases include those caused by invading microbes or parasites. As used herein, "microbe" denotes virus, bacteria, rickettsia, mycoplasma, protozoa, fungi and like microorganisms, "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like, including helminths, while "infectious agent" or "pathogen" denotes both microbes and parasites.

The protein substances useful in the methods of the present invention include protein, peptide, polypeptide, glycoprotein, lipoprotein, or the like, e.g. hormones, lymphokines, growth factors, albumin, cytokines, enzymes, immune modulators, receptor proteins, antibodies and antibody fragments.

The protein substance of particular interest in the present invention are antibodies and antibody fragments. By "antibodies and antibody fragments" is meant generally immunoglobulins or fragments thereof that specifically bind to antigens to form immune complexes.

The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention. It is will be appreciated that newer techniques for production of monoclonals can also be used, e.g., human monoclonals, interspecies monoclonals, chimeric (e.g., human/mouse) monoclonals, genetically engineered antibodies and the like.

Antibody fragments useful in the present invention include $F(ab')_2$, $F(ab)_2$, Fab', Fab, Fv and the like including hybrid fragments. Preferred fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin. The fragments may also be produced by genetic engineering.

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating lesions and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the targeted lesion. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., *Immunol. Today,* 5,299(1984).

Preferred are proteins having a specific immunoreactivity to a marker substance of at least 60% and a cross-reactivity to other antigens or non-targeted substances of less than 35%.

As disclosed above, antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846. In particular, antibodies against an antigen, e.g., a gastrointestinal, lung, breast, prostate, ovarian, testicular, brain or lymphatic tumor, a sarcoma or a melanoma, are advantageously used.

A wide variety of monoclonal antibodies against infectious disease agents have been developed, and are summarized in a review by Polin, in Eur. J. Clin. Microbiol., 3(5):387–398, 1984, showing ready availability. These include monoclonal antibodies (MAbs) against pathogens and their antigens such as the following:

Anti-bacterial Mabs

Streptococcus agalactiae
Legionella pneumophilia
Streptococcus pyogenes
Esherichia coli
Neisseria gonorrhosae
Neisseria meningitidis
Pneumococcus
Hemophilis influenzae B
Treponema pallidum
Lyme disease spirochetes
Pseudomonas aeruginosa Mycobacterium leprae
Brucella abortus
Mycobacterium tuberculosis
Tetanus toxin Anti-viral MAbs HIV-1, -2, -3
Hepatitis A, B, C, D
Rabies virus
Influenza virus
Cytomegalovirus
Herpes simplex I and II
Human serum parvo-like virus
Respiratory syncytial virus
Varicella-Zoster virus
Hepatitis B virus
Measles virus
Adenovirus
Human T-cell leukemia viruses
Epstein-Barr virus
Murine leukemia virus*
Mumps virus
Vesicular stomatitis virus
Sindbis virus
Lymphocytic choriomeningitis virus
Wart virus
Blue tongue virus
Sendai virus
Feline leukemia virus*
Reo virus
Polio virus
Simian virus 40*
Mouse mammary tumor virus*
Dengue virus
Rubella virus
*=animal virus Anti-protozoan MAbs Plasmodium falciparum
Plasmodium vivax
Toxoplasma gondii
Trypanosoma rangeli
Trypanosoma cruzi
Trypanosoma rhodesiensei
Trypanosoma brucei
Schistosoma mansoni
Schistosoma japanicum
Babesia bovis
Elmeria tenella
Onchocerca volvulus
Leishmania tropica
Trichinella spiralis
theileria parva
Taenia hydatigena
Taenia ovis
Taenia saginata
Echinococcus granulosus
Mesocestoides corti Antimycoplasmal MAbs Mycoplasma arthritidis
M. hyorhinis
M. orale
M. arginini
Acholeplasma laidlawii
M. salivarium
M. pneumonia Additional examples of MAbs generated against infectious organisms that have been described in the literature are noted below.

MAbs against the gp 120 glycoprotein antigen of human immunodeficiency virus 1 (HIV-1) are known, and certain of such antibodies can have an immunoprotective role in humans. See, e.g., Rossi et al., Proc. Natl. Acad. Sci. USA, 86:8055–8058, 1990. Other MAbs against viral antigens and viral induced antigens are also known. This shows that proper selection of the epitope can distinguish between a therapeutic and non-therapeutic target.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207:71–73, 1980).

Several groups have developed MAbs to T. gondii, the protozoan parasite involved in toxoplasmosis (Kasper et al., J. Immunol. 129:1694– 1699, 1982; Id., 30:2407–2412, 1983).

MAbs have been developed against schistosomular surface antigens and have been found to act against schistosomulae in vivo or in vitro (Simpson et al., Parasitology, 83:163–177, 1981; Smith et al., Parasitology, 84:83–91, 1982; Gryzch et al., J. Immunol., 129:2739–2743, 1982; Zodda et al., J. Immunol. 129:2326–2328, 1982; Dissous et al., J. Immunol., 129:2232–2234, 1982).

Trypanosoma cruzi is the causative agent of Chagas' disease, and is transmitted by blood-sucking reduviid insects. A MAb has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639–640, 1982).

Suitable MAbs have been developed against most of the microorganisms (bacteria, viruses, protozoa, other parasites) responsible for the majority of infections in humans, and many have been used previously for in vitro diagnostic purposes. These antibodies, and newer MAbs that can be generated by conventional methods, are appropriate for use in the present invention.

Proteins useful for detecting and treating cardiovascular lesions include fibrin-specific proteins, for example, fibringen, soluble fibrin, antifibrin antibodies and fragments, fragment $E_1$ (a 60 kDa fragment of human fibrin made by controlled plasmin digestion of crosslinked fibrin), plasmin (an enzyme in the blood responsible for the dissolution of fresh thrombi), plasminogen activators (e.g., urokinase, streptokinase and tissue plasminogen activator), heparin, and fibronectin (an adhesive plasma glycoprotein of 450 kDa) and platelet-directed proteins, for example, platelets, antiplatelet antibodies and antibody fragments, anti-activated platelet antibodies, and anti-activated-platelet factors, which have been reviewed by Koblik et al., Semin. Nucl. Med., 19:221–237 1989, all of which is included herein by reference.

Among the diagnostic and therapeutic agents useful in the methods of the present invention, gamma-emitters, positron-emitters, x-ray emitter, paramagnetic ions and fluorescence-emitters are suitable for detection and/or therapy, while beta- and alpha-emitters and neutron-capturing agents, such as Boron and Uranium, also can be used for therapy.

Suitable radioisotopes for the methods of the present invention include: Actinium-225, Astatine-211, Iodine-123, Iodine-125, Iodine-126, Iodine-131, Iodine- 133, Bismuth-212, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-186, Rhenium-188, Tellurium- 121m, Tellurium-122m, Tellurium-125m, Thulium-165, Thulium-167, Thulium- 168, Technetium-99m, Fluorine- 18, Silver-111, Platinum-197, Palladium-109, Copper-67, Phosphorus-32, Phosphorus- 33, Yttrium-90, Scandium-47, Samarium-153, Lutetium-177, Rhodium-105, Praseodymium-142, Praseodymium-143, Terbium-161, Holmium-166, Gold-199, Cobalt-57, Cobalt-58, Chromium-51, Iron-59, Selenium-75, Thallium-201, and Ytterbium-169. Preferably the radioisotope will emit a particle or ray in the 10–7,000 kev range, more preferably 50–1,500 kev.

Isotopes preferred for external imaging include: Iodine-123, Iodine- 131, Indium- 111, Gallium-67, Ruthenium-97, Technetium-99m, Cobalt-57, Cobalt-58, Chromium- 51, Iron-59, Selenium-75, Thallium-201, and Ytterbium-169.

Isotopes most preferred for internal detection include: Iodine-125, Iodine-123, Iodine-131, Indium-111, Technetium-99m and Gallium-67.

Isotopes preferred for therapeutic use include: Actinium-225, Bismuth-212, Lead-212, Bismuth- 213, Iodine-125, Iodine-131, Rhenium- 186, Rhenium-188, Silver-111, Platinum-197, Palladium-109, Copper-67, Phosphorus- 32, Phosphorus-33, Yttrium-90, Scandium-47, Samarium-153, Lutetium-177, Rhodium- 105, Praseodymium-142, Praseodymium-143, Terbium- 161, Holmium-166, and Gold- 199.

Among the therapeutic agents useful in the current invention are isotopes, drugs, toxins, fluorescent dyes activated by nonionizing radiation, hormones, hormone antagonists, receptor antagonists, enzymes or proenzymes activated by another agent, autocrine or cytokine. Many drugs and toxins are known which have cytotoxic effects on cells. They are to be found in compendia of drugs and toxins, such as the Merck Index, Goodman and Gilman, and the like, and in the references cited above. Any such drug can be conjugated to or loaded onto the protein, polymer or biotin/avidin by conventional means well know in the art, and illustrated by analogy to those described above.

The present invention also contemplates dyes used, for example, in photodynamic therapy, conjugated to proteins, biotin or avidin and used in conjunction with appropriate nonionizing radiation.

The use of light and porphyrins in methods of the present invention is also contemplated and their use in cancer therapy has been reviewed by van den Bergh (Chemistry in Britain, May 1986, Vol. 22, pp. 430– 437), which is incorporated herein in its entirety reference.

Examples of known cytotoxic agents useful in the present invention are listed in Goodman et al., "The Pharmacological Basis of Therapeutics," Sixth Edition, A. G. Gilman et al, eds./Macmillan Publishing Co. New York, 1980. These include taxol; nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used in the methods of the present invention; such drugs are known to these skilled in the art and include puromycin, cycloheximide, and ribonuclease.

Toxins can also be used in the methods of the present invention. Toxins useful as therapeutics are known to those skilled in the art and include plant and bacterial toxins, such as, abrin, alpha toxin, diphtheria toxin, exotoxin, gelonin, pokeweed antiviral protein, ricin, and saporin.

Toxins in their native form require a minimum of three different biochemical functions to kill cells: a cell binding function, a cytotoxic function, and a function to translocate the toxic activity into the cells.

The modified toxins useful in the present invention differ from native toxins in that the domain providing the cell binding function of the native toxin is nonfunctioning because the domain is missing partially or totally.

Other therapeutic agents useful in the present invention include anti-DNA, anti-RNA, radiolabeled oligonucleotides, such as anti-sense oligodeoxy ribonucleotides, anti-protein and anti-chromatin cytotoxic or antimicrobial agents.

The proteins useful in the methods of the present invention may be labeled or conjugated by a variety of methods known in the art. Many of these methods are disclosed in the above-referenced U.S. Patents and Patent Applications. See also, Rayudu, op. cit.; and Childs et al., *J. Nuc. Med.*, 26, 293( 1985). Any conventional method of radiolabeling which is suitable for labeling isotopes for in vivo use will be generally suitable for labeling detection agents according to the present invention.

The avidin or biotin may be conjugated to therapeutic agents such as drugs; toxins; agents useful in neutron capture therapy, such as boron and uranium; isotopes; fluorescent dyes activated by nonionizing radiation; hormones; autocrines; enzymes and proenzymes activated by another agent; cytokines; cytoprotective agents; etc., by methods known to those skilled in the art. U.S. Pat. No. 5,057,313, Shih et al, hereby incorporated by reference, teaches one such method.

Other examples of methods of conjugating avidin to a detection or therapeutic agent include the following: (a) the chloramine-T or Bolton-Hunter procedures for conjugating iodine, (b) the procedures described by Griffiths et al. (Cancer Res. 51:4594, 1991) or Fritzberg et al. (U.S. Pat. No. 5,120,526) to conjugate technetium or rhenium (c) through bifunctional chelating agents as described by Meares et al. (Br. J. Cancer 62:21, 1990) to conjugate metallic nuclides. Additionally, avidin or biotin can be bound to dendrimers by procedures described for amino-containing proteins as described by Hnatowich et al. (J. Nucl. Med. 28:1294, 1987).

Biotin can be readily conjugated to proteins (including antibodies and their fragments) via the proteins' lysine and cysteine residues, and, if available, their oxidized carbohydrate groups. These methods are exemplified below.

Methods which can be used to conjugate biotin or avidin to dextran include those described in Shih et al. U.S. Pat. No. 5,057,313, which is hereby incorporated by reference, for conjugating haptens containing suitable derivatives groups to dextrans.

One method for the conjugation of biotin to a starburst dendrimer is to treat a generation 3 to generation 10 starburst dendrimer solution (0.01 to 100 mmol) in tris, hepes, phosphate, carbonate or borate buffer (1 to 2000 mmol) with a solution of N-hydroxysuccinimidobiotin or N-hydroxysulfosuccinimidobiotin (0.01 mmol to 10 mol). A co-solvent such as DMF or DMS) may be added in amounts up to 70% to facilitate solubility. The reaction is allowed to proceed for 0.25 to 24 hours at 4°–100° C. The substituted polymer is purified by dialysis and/or size-exclusion or ion-exchange chromatography. The substitution ratio or biotin to polymer is determined with the HABA reagent and a standard photometric determination of free amino groups, for example with flourescamine or ninhydrin.

One method for conjugating avidin to a starburst dendrimer is to treat a generation 3 to generation 10 starburst dendrimer (0.01 to 100 mmol) with maleic anhydride (0.01 to 1000 mmol) in a suitable solvent such as DMF, toluene or DMSO with the optional addition of a base such as potassium carbonate or sodium hydride. The reaction is allowed to proceed for 1 to 96 hours at a temperature of 25° to 170° C., optionally with a device for the removal of water formed during the reaction, to drive the reaction to completion. This and similar reaction conditions are well known and described in the literature (Hargreaves et al. Chem. Rev. 70:439– 469, 1970),. The reaction mixture is purified by size-exclusion or ion-exchange chromatography and/or dialysis in a buffer below pH 7, to preserve maleimide groups. The substitution ratio of maleimide onto the dendrimer is determined spectrophotometrically through the absorbance of the conjugated imide and quantitation of amino-groups pre- and post-reaction with reagents such as flourescamine and ninhydrin. Avidin is either reduced with a thiol agent such as 2-mercaptoethanol, to cleave a limited number of disulfide bonds (Griffiths et al. Cancer Res. 51:4594–4602, 1991 ) or reacted with a reagent which is known to insert free thiol groups into proteins. For example, in the latter method, a solution of avidin (0.001 to 1000 mmol) in tris, hepes, borate, carbonate or phosphate buffer, ph 6to 10, is treated with a solution of 2-iminothiolane (0.0001 to 1000 mmol). The reaction is allowed to proceed for 0.25 to 24 hours at 4° to 50° C. The substituted avidin is purified as above and the number of thiol groups determined by the Ellman reaction (Ellman, *Arch. Biochem. Biophys.* 82:70–77, 1959).

The maleimide-dendrimer (0.001 to 100 mmol) and the thiol-avidin (0.001 to 100 mmol) are mixed together in a suitable buffer at a pH of 5–8 for 0.25 to 24 hours at 4° to 50° C. The conjugates are purified by size-exclusion, ion-exchange, affinity, and/or hydrophobic interaction chromatography according to the exact nature and size of the polymeric reactants. Conjugates are sized by native/SDS gels and analyzed for biotin-binding capability with the HABA reagent, as described above.

Methods of preparing conjugates of multiavidin/biotin with polymer and active agent are known to those skilled in the art. One method is illustrated in the examples below.

A physiological solution of the protein containing conjugate is advantageously metered into sterile vials, e.g., at a unit dosage of about 1.0– 500 mg protein conjugate/vial, and the vials are either stoppered, sealed and stored at low temperature, or lyophilized, stoppered, sealed and stored.

In an embodiment of the detection or therapeutic protocol of the present invention, the biotin-polymer-protein conjugate can be injected parentally, usually at a protein dose of 0.5 to 200 mg. This can be administered as a single injection or in divided doses. After 1–5 days, more preferably at less than 2 days and even at less than 1 day when the first agent involves a small and rapidly targeting molecule, such as an antibody fragment or subfragment, a dose of unlabeled clearing agent, such as 2.0 to 200.0 mg avidin is administered parenterally. The clearing agent and localizing agent can be given as a single injection or in divided doses; administering the clearing agent and localizing agent in two doses is preferred in certain circumstances. The third step involves injection of the biotin conjugated to a detection or therapeutic agent. The third step's reagents can be administered parenterally within 24 hrs of the 2nd step, but also at up to 3 days later. In one detection embodiment, the third step involves 111-In conjugated to biotin attached to a lesion-targeting antibody or antibody fragment. Within 24 hours of the last injection, more preferably within 4 hours, planar and single-photon emission computed tomography scans are made with a gamma camera equipped with the appropriate collimator and selecting the appropriate energy windows for the detection isotope being used, such as 173 keV and 247 keV for 111-In.

In another embodiment of the detection or therapy protocol of the present invention, the biotin-lesion-targeting protein conjugate can be injected parenterally, usually at a protein dose of 2 to 200 mg, more preferably within a dose range of 5 to 50 mg. This can be administered as a single or as divided injections. After 1–5 days, more preferably at less than 2 days and even at less than 1 day when the first agent involves a small and rapidly targeting protein, such as an antibody fragment or subfragment, a dose of a multiavidin-polymer conjugate clearing agent is given parenterally. The longer the delay after the first step, the lower the amount (and ratio) of clearing agent and localizing agent given. The clearing agent and the localizing agent can be given as a single injection or in divided doses, dividing the administration of the clearing agent and localizing agent into at least 2 doses may be preferable, usually within a short period, such as within 2 hrs. In the third step of this embodiment of the invention, a dose of 2 to 200 mg of biotin conjugated with a detection or therapeutic agent, as appropriate, is administered parenterally either as a single dose or in divided doses.

Variations and modifications of these formulations will be readily apparent to the ordinary skilled artisan, as a function of the individual needs of the patient or treatment regimen, as well as of variations in the form in which the radioisotopes may be provided or may become available.

Routes of administration for the composition include intravenous, intraarterial, intrapleural, intraperitoneal, intrathecal, subcutaneous or by perfusion.

An application for the method of the present invention is for magnetic resonance imaging (MRI). In this case, for example, a suitably radiolabeled conjugate or a conjugate bearing a mr image enhancing agent is administered with the intention of obtaining an image of the lesion.

The method of the invention can be practiced either with scintigraphic or magnetic resonance imaging agents. A combination of these imaging agents can also be used, although this requires more complex instrumentation and data processing.

Scintigraphic imaging according to the method of the invention is effected by obtaining a scintigram of the lesion of interest.

The scintigram is normally taken by a gamma imaging camera having one or more windows for detection of energies in the 50–500 keV range. Use of radioisotopes with higher energy, beta, or positron emissions would entail use of imaging cameras with the appropriate detectors, all of which are conventional in the art.

The scintigraphic data can be stored in a computer for later processing.

Methods useful for internal detection and/or treatment of tumors and/or other lesions are disclosed in U.S. Pat. No. 4,782,840; U.S. Pat. No. 4,932,412; and copending U.S. patent application Ser. No. 07/879,857, the disclosures of which are incorporated herein by reference. The methods of the present invention can be used to enhance the methods disclosed in these references.

Magnetic resonance imaging (MRI) is effected in an analogous manner to scintigraphic imaging except that the imaging agents will contain magnetic resonance (mr) enhancing species rather than radioisotopes. It will be appreciated that the magnetic resonance phenomenon operates on a different principle from scintigraphy. Normally, the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, *Scientific American,* 246, 78 (1982); Runge et al., *Am. J. Radiol.,* 141, 1209(1983).

The MR image enhancing agent must be present in sufficient amounts to enable detection by an external camera, using magnetic field strengths which are reasonably attainable and compatible with patient safety and instrumental design. The requirements for such agents are well known in the art for those agents which have their effect upon water molecules in the medium, and are disclosed, inter alia, in Pykett, op. cit., and Runge et al., op. cit.

MRI contrast agents are well known in the art and include, for example, Gadolinium, Iron, Manganese, Rhenium, Europium, Lanthanium, Holmium, and Terbium.

The MR scans are stored in a computer and the images processed analogously to the scintigraphic data.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Accordingly, these embodiments constitute improved methods and reagents for amplification of therapeutic or detection agents at a lesion targeted for detecting and therapy especially of cancer and other pathological conditions.

EXAMPLES

Example 1—Conjugating an Antibody or Antibody Fragment to Biotin a) Via a lysine residue An antibody or antibody fragment at a concentration of 1–20 mg/ml in a non-amine containing buffer (e.g., borate, phosphate, etc.), at a suitable concentration (0.05– 0.5M), at a slightly elevated pH (7.0–9.5), is mixed with a 1–100 molar excess of the activated ester (succinimide or sulfosuccinimide are preferred) of D-biotin or D-biotin incorporating a spacer arm (such as succinimido- 6-[biotinamido] hexanoate). A cosolvent, such as dimethylformamide (DMF) or dimethylsulfoxide (DMSO), may be added to provide a final concentration of up to 20% to facilitate reactant solubility. The reaction solution is stirred for 1–24 hours and kept at a temperature of 4° C. to 37° C. At the end of the reaction period, the modified protein is separated from unbound biotin and other low molecular weight contaminants by size-exclusion chromatography and/or dialysis.

b) Via a Cysteine Residue

An antibody or antibody fragment at a concentration of 5–20 mg/ml in 0.1–0.5M tris buffer, pH 8.7, is made 0.5–5 mg/ml in 2-mercaptoethanol. The reaction solution is let stand for 5–120 minutes at a temperature of 4°– 37° C. The reduced protein is separated from unreacted thiol by size-exclusion chromatography in 50 mM acetate buffer, pH 4.5. Protein concentration and the number of thiol groups per antibody molecule may be determined at this time. The reduced antibody or antibody fragment at a concentration of 1–20 mg/ml in a non-amine containing buffer (e.g., phosphate) at a neutral pH (5.0–7.0) is mixed with a 1–100 molar excess of biotin-maleimide (N-biotinyl-N-[6-maleimido hexanoyl]hydrazide) (Sigma Chem. Co). A co-solvent, e.g., DMF or DMSO, may be added to provide a final concentration of up to 20% to facilitate reactant solubility. The reaction solution is stirred for 1–24 hours at a temperature between 4°–37° C. At the end of the reaction period, the biotinylated protein is separated from unbound biotin and other low molecular weight contaminants by size-exclusion chromatography and/or dialysis.

c) Via a Carbohydrate Moiety

Antibody or antibody fragment at a concentration of 1–20 mg/ml is treated with sodium metaperiodate to a final concentration of 0.1–10 mg/ml in phosphate buffered saline at room temperature for 1–4 hours. Ethylene glycol is added to decompose the remaining periodate. The oxidized IgG is purified from low molecular weight contaminants by size-exclusion chromatography in phosphate buffer. The oxidized antibody (1–20 mg/ml) is reacted with a 1–100 molar excess of biotin-hydrazide (Pierce Chemical Co.) in a non-amine buffer (e.g., phosphate, carbonate, etc.) at neutral pH (5.0–8.0) for 1–48 hours at 4°–37° C. After the optimum time for coupling, the formed hydrazones are reduced by the addition of sodium cyanoborohydride with pH adjustment to >7. The biotinylated antibody is purified by size-exclusion chromatography and/or dialysis.

d) Via Addended Thiol Groups

An antibody or antibody fragment at a concentration of 1–20 mg/ml in a non-amine containing buffer (e.g., borate, carbonate, etc.)at a suitable concentration (0.05–0.5M) and pH (7–10) is mixed with a 1–100 molar excess of 2-iminothiolane hydrochloride (Pierce Chemical Co.). The reaction mixture is made 1–100 mM in EDTA to help prevent disulfide bond formation and held at 4°– 37° for from 1–4 hours. The modified protein is purified by size-exclusion chromatography in a neutral to slightly acidic buffer (e.g., acetate, titrate, etc.) pH 5.0–7.0. The purified sulfhydryl substituted antibody (1–20 mg/ml) is mixed with a 1–100 molar excess of biotin maleimide. A co-solvent, e.g., DMF or DMSO, may be added to a final concentration of up to 20% to facilitate reactant solubility. The reaction solution is stirred for 1–24 hours at a temperature between 4°–37° C. At the end of the reaction period, the biotinylated protein is separated from unbound biotin and other low molecular weight contaminants by size-exclusion chromatography and/or dialysis.

e) Site-Specific Conjugation of Biotin and Fab' Fragments

An antibody $F(ab')_2$ fragment (obtained by pepsin digestion of the intact antibody) at a concentration of 5–20 mg/ml in phosphate buffer at pH 6–8 is treated with a fleshly prepared solution of L-cysteine to give a final cysteine concentration of 1–50 mg/ml. The reaction is allowed to proceed for 1–4 hours at 25°–37° C. At the end of this period, the Fab' fragment is purified from low molecular weight contaminants by size-exclusion chromatography in an acidic buffer (e.g., acetate, etc.) at pH 4.0–6.0. The Fab' fragment is reacted with a 1–100 molar excess of biotin-maleimide at pH 5.0–7.0. A co-solvent, e.g., DMF or DMSO, may be added to a final concentration of up to 20% to facilitate reactant solubility. The reaction is stirred for 1–24 hours at a temperature between 4°–37° C. At the end of the reaction period, the biotinylated antibody fragment is separated from unbound biotin and other low molecular weight contaminants by size-exclusion chromatography and/or dialysis.

f) Determination of Extent of Biotinylation of Proteins

A small amount of biotinylated antibody is heated to 560 in 0.1M phosphate buffer for 10 minutes and enzymatically digested with small volumes of 1% pronase (Sigma Chemical Co.). The digestion is allowed to proceed overnight. The digest is analyzed with a 10 uM solution of avidin saturated with a 100 uM solution of 2-(4'-hydroxyazobenzene)-benzoic acid (HABA) in 0.1M phosphate buffer, pH 7.0. The avidin-HABA solution is titrated with increasing volumes of digested biotinylated antibody as well as a standard biotin solution containing 1–10 mM of biotin. The change in absorbance at 500 nM for each is determined, and the concentration of biotin in the pronase digested biotinylated antibody calculated from reference to the standard curve of the titration of biotin with avidin-HABA.

Example 2—Preparation of a multibiotin-starburst dendrimer-antibody Fab' fragment conjugate 0.001 mol of a multibiotinylated-starburst dendrimer in Tris.HCl buffer (0.1M, pH 8.0, 1 ml) prepared as described generally in the specification above, is reacted with a solution of bromoacetyl chloride (0.02 mmol) in dimethyl sulfoxide (DMSO, 0.2 ml) by the dropwise addition of the latter over 1 hour with stirring. The reaction is stirred at room temperature for a further 1 hour and the dendrimer purified on a G-10 size exclusion column. A Fab' fragment of a monoclonal antibody which binds to colon-specific antigen p is prepared by reduction of a 20 mg/ml solution of the $F(ab')_2$ fragment with a 50 mg/ml solution of L-cysteine in phosphate buffered saline (PBS), 40 mM, pH 7.4, for 1 hour at 37° C., and subsequent purification of the Fab' fragment on an acrylamide column run in acetate buffered saline (ABS) 0.1M, pH 4.5. The Fab' fragment assays for 2–3 free thiol groups per Fab' when analyzed with dinitrodithiobenzoic acid (DTNB) by the method of Ellman.

The bromoacetyl multibiotinylated dendrimer (0.0005 mmol) is mixed with a solution of the reduced antibody Fab' fragment (0.0005 mmol) in Tris. HCl buffer, 0.1M, pH 7.5, and the solution stirred at room temperature for 3 hours. The Fab'$(biotin)_n$-dendrimer conjugate is purified on a bed of S-sepharose equilibrated in 50 mM sodium acetate and run in a gradient of 0 to 1M sodium chloride.

Example 3—Preparation of multibiotinylated 40 kilo Dalton dextran

A—One gram of dextran (40 kD MW) is partially oxidized with sodium periodate (0.33 g) by stirring them together for 1 hour in the dark at room temperature. The polyaldehyde dextran so formed is purified by buffer exchange with an Amicon filter unit and lyophilized to give a white powder.

The polyaldehyde dextran (0.02 mmol) is then reacted with biotin hydrazide (1 mmol) at room temperature for 4 hours in PBS buffer, 0.1M, pH 7.5, to form hydrazone derivatives. The hydrazones are reduced by the addition of sodium borohydride (3 mmol) and stirring for 2 hours at room temperature. The biotinylated dextran is then purified on a G-25 gel-filtration column run in 50 mM ABS to eliminate low MW contaminants. The biotin substitution level is estimated by the HABA test procedure and confirmed by titration against an accurately measured amount of avidin.

B—In alternative procedure, the polyaldehyde dextran (0.02 mmol) is reacted with 1,3-diamino-2-hydroxypropane (2 mmol) at room temperature for 24 hours and then treated with sodium borohydride (3 mmol) for a further 2 hours at room temperature. The amino-dextran is purified on a G-25 size-exclusion column run in 50 mM ABS, pH 4.5, and the amino-substitution determined spectrophotometrically by reaction with trinitrobenzenesulfonic acid (TNBS). An amino substitution level of 50 to 100 per dextran is obtained when assayed against an amino reference compound. The amino dextran (0.001 mmol) is then reacted with an N-hydroxysuccinimide ester of biotin (0.05 mmol) at a pH of 8 for 24 h at 25° C. The (biotin) dextran is then separated from the low MW contaminants on a G-25 size-exclusion column run in 50 mM ABS, pH 4.5. The biotin substitution ratio is determined with the HABA method, verified by avidin titration, and further confirmed by TNBS determination of remaining unreacted amino groups.

Example 4—Preparation of multibiotin-dextran-antibody conjugates

A—The biotinylated amino-dextran (0.001 mmol) prepared in example 3b is treated with a solution of bromoacetyl chloride (0.01 mmol) at a pH of 7.5 for 2 h at 25° C. The modified biotinylated dextran is purified on an acrylamide size-exclusion column prior to reaction with an antibody containing free sulfhydryl groups.

The antibody sulfhydryl groups are produced by an antibody reduction with a thiol agent. The antibody at 20 mg/ml in TRIS.HCl buffer, 0.1M, pH 8.7, is treated with 2-mercaptoethanol to a final concentration of 25 mM. The reaction is stirred at 4 degrees for 10 minutes and the reduced protein is purified by size-exclusion chromatography. The antibody concentration is determined and the ratio of sulfhydryl groups per mole of antibody determined by the Ellman reaction, using dithiodinitrobenzoic acid (DTNB), by reference to a standard curve. The reduced antibody containing 2–3 free thiol groups is mixed with the bromoacetyl-biotin-dextran derivative, prepared as above and containing a limited number of bromoacetyl groups, in a 1:2 ratio at a pH of 7.5 for 3 hours at 37° C. The conjugate is purified by ion-exchange and/or size-exclusion and/or hydrophobic interaction chromatography (HIC) and analyzed by HPLC, and for biotin content and antibody concentration in similar procedures as described above. The conjugate is assayed for immunoreactivity retention with its pertinent antigen and for quantitative avidin binding ability.

B—In an alternate method, the required free thiol groups on the antibody or fragment may be obtained by substituting the protein with 2-iminothiolane as described in the literature (Blattler et al. *Biochemistry,* 24:1517– 1524, 1985), and proceeding as described above for the analysis of the thiol-antibody, its conjugation to the biotin-dextran, and the subsequent purifications and analyses.

Example 5—Preparation of multiavidin-dextran conjugate

Polyaldehyde dextran (0.001 mmol) and avidin (0.03 mmol) are mixed together and stirred at 25° C. for 16 hours at a pH of 7 in 40 mM PBS. Conjugation progress is followed by a suitable analytical procedure such as size-exclusion or HIC HPLC. The reaction mixture is treated with sodium borohydride (0.05 mmol) for 2 hours at room temperature at a pH of 8 in 40 mM PBS, to convert the imine groups to amino groups and thus fix the avidin units to the dextran backbone. The (avidin) $_n$-dextran conjugates containing 2 and 3 avidin units per dextran are separated from each other and the rest of the reaction mixture by ion-exchange chromatography on S-sepharose equilibrated in 50 mM acetate buffer and run in a gradient of 0 to 2M sodium chloride. The biotin binding capability of the purified avidin conjugates is determined using the HABA test and a quantifiable amount of biotin conjugated to a fluorescent agent or radioisotope. The conjugates are further analyzed by polyacrylamide gel electrophoresis to verify the presence of 2 and 3 avidin units per dextran for the isolated products, respectively.

Example 6—Preparation of an (avidin)$_2$-dextran, Fab' conjugate

The (avidin)$_2$ dextran conjugate prepared above (0.0005 mmol) in 1 ml of 0.1M Tris.HCl buffer, pH 8, is treated with 100 ul of a solution of bromoacetyl chloride (0.005 mmol) in DMSO with rapid stirring at 4° C. The mixture is stirred for 30 minutes and the modified polymer is purified on an acrylamide size-exclusion column run in 40 mM PBS, pH 7.5. The F(ab')$_2$ fragment of an antibody which binds to the carcinoembryonic antigen, (designated NP-4 in Hansen et al., *Proc. Am. Assoc. Cancer Res,* 30:414, 1989) in 40 mM PBS, pH 7.4, is treated with L-cysteine, to a final cysteine concentration of 100 mmol, for 1 hour at 37° C. The Fab' is purified on an acrylamide column run in 50 mM ABS, pH 4.5, and assayed for thiol concentration per mole of Fab' by the Ellman reaction and absorbance at 280 nm, respectively. The Fab' (0.0005 mmol) and bromoacetyl-(avidin)$_2$-dextran (0.0005 mmol) are mixed together in 50 mM PBS buffer, pH 7.5, and stirred at 25° C. for 3 hours. The product, Fab'-(avidin)$_2$-dextran, is purified from uncoupled reactants by ion-exchange chromatography on S-sepharose equilibrated in 50 mM acetate buffer, pH 4.5, run in a gradient of 0 to 2M sodium chloride.

Example 7—Preparation of a multibiotin-dextran-doxorubicin conjugate

Polyaldehyde dextran (0.02 mmol), prepared as described above, and containing 10–200 aldehyde functionalities is treated with biotin-hydrazide (0.1 mmol) at a pH of 6 for 2 hours at room temperature. Remaining free aldehyde groups are reacted with doxorubicin (1 mmol) under similar conditions and the imino groups converted to amino groups by reduction by the addition of sodium borohydride (2 mmol) and reaction over a period of 4 hours at pH 8. The conjugate product is purified by size-exclusion chromatography on a G-10 column, equilibrated in 50 mM ABS, pH 4.5.

Analyzing the conjugate indicates approximately 5 biotin residues per dextran by the HABA test, and for approximately 35 doxorubicin moieties when tested spectrophotometrically at 496 nm.

Example 8—Conjugation of biotin to a bifunctional chelating agent to form a conjugate useful to deliver an active metal agent therapeutic or detection agent.

Biotinylpentylamine (0.001 mol) and isothiocyanatobenzyl-diethylenetriamine-pentaacetic acid (ITC-DTPA, 0.001 mol) are mixed together in borate buffer, 0.1M, pH 8, and stirred for 3 hours at room temperature. The biotin-DTPA is purified on a C-18 reverse-phase HPLC column run in an acetonitrile/water gradient. The acetonitrile is removed under reduced pressure on a rotary evaporator and the water by lyophilization to give a white powdery product. The structure, biotinylpentylamino-thioureaylbenzyl-DTPA (biotin-DTPA) is confirmed by mass spectral and micro analysis.

Example 9—Yttrium-90 radiolabeling of the biotin-DTPA conjugate of Example 8

A 25 mCi sample of yttrium-90 chloride in 0.05M HCl is treated with an equal volume of 0.5M sodium acetate buffer, pH 5, to convert the metal to its acetate salt. The mixture is allowed to stand for 10 minutes at room temperature. A 250 ug sample of biotin-DTPA in sodium acetate buffer, 50 mM, pH 6, is then added. The components are mixed and allowed to stand for 30 min., at which time analysis by instant thin-layer chromatography (ITLC) run in water/ethanol/5N ammonium hydroxide (which will precipitate unchelated yttrium) indicates that 99% of the yttrium-90 is bound to the biotin-DTPA. The $^{90}$Y-DTPA-biotin is then ready to use.

Example 10—Conjugation of biotin and a bifunctional chelating agent to a polymer to provide a (biotin)$_n$(bifunctional chelating agent)$_m$ -polymer useful for targeting metalic detection or therapeutic agents Polyaldehyde dextran (0.02 mmol) prepared as in example 3a, is treated with biotinylpentylamine (0.1 mmol) at a pH of 8 for 2 hours at room temperature. 2-hydroxy-1,3-diaminopropane (2 mmol) is added and the solution stirred for a further 3 hours. Sodium borohydride (4 mmol) is added and the reaction is stirred for a further 3 hours at room temperature. The product is purified on a G-10 size-exclusion column to give a dextran substituted with approximately 5 biotin residues and 100 free amino groups, as analyzed by HABA testing and TNBS assays. The (biotin)$_5$-aminodextran (0.01 mmol) is treated with a solution of ITC-DTPA (0.5 mmol) in 0.1M borate buffer, pH 8, for 6 hours at room temperature. The product is purified from unbound DTPA derivatives by G-10 size-exclusion chromatography and dialysis. The number of DTPA residues per dextran is found to be approximately 40 by spectrophotometric determination at 254 nm, verified by cobalt-57 radiolabeling of the conjugate using various excess amounts of cobalt-57.

Example 11—Yttrium-90 radiolabeling of $(biotin)_5(DTPA)_{40}$-dextran

Yttrium-90 chloride (25 mCi) is converted to its acetate form as described in example 9 and then treated with $(biotin)_5(DTPA)_{40}$-dextran (0.0001 mmol) under the same conditions used in the monomer preparation in example 9. ITLC showed 99% of the yttrium to be chelated by the conjugate after a 30 minute radiolabeling. The $^{90}Y$-$(DTPA)_{40}(biotin)_5$-dextran is then ready for use.

Example 12—Cancer Imaging with Three-Step Procedure

A patient diagnosed by sigmoidoscopy to have a colonic neoplasm is injected i.v. with composition comprised of conjugate of multibiotin-starburst dendrimer-monoclonal antibody IgG against carcinoembryonic antigen (CEA). Two days later, unlabeled avidin (in two divided doses, 20 min apart) is injected i.v. The next day, biotin labeled with 111-In (4 mCi) is injected i.v. The patient is scanned with a gamma camera 2 hours later, and a focus of increased radioactivity is detected in the region of the sigmoid colon, in agreement with the sigmoidoscopy findings.

Example 13—Atherosclerotic Imaging with Three-Step Procedure

A patient with suspected atherosclerotic plaques in various arteries is injected i.v. with a composition comprised of a conjugate of multibiotin-dextran-monoclonal antibody $F(ab')_2$ against macrophage. One day later, a multiavidin-dextran conjugate (in two divided doses, 15 min apart) is injected i.v. One day later, biotin conjugated with 5 mCi of 111-In is injected i.v., and the patient scanned with a gamma camera 3 hours later. Foci of abnormal radioactivity is found.

Example 14—Cancer Radioimmunotherapy with a Four-Step Procedure

A patient with several small colonic carcinoma metastases to the liver is injected i.v. with a first composition comprised of a conjugate of multiavidin-dextran-anti-CEA IgG monoclonal antibody. Two days later, a clearing composition of biotin is injected i.v., followed 30 minutes later by the i.v. injection of a localized composition of multibiotin-dextran. After another 2 days, a composition of multiavidin-dextran labeled with I-131 is injected i.v. Two weeks later, a second therapy dose of a composition of biotin-DTPA-Y90 is given i.v.

Example 15—Cancer Chemoimmunotherapy with a Four-Step Procedure

A patient with a fight lung adenocarcinoma is injected i.v. with a conjugate of multibiotin, dextran and antilung-cancer IgG. Four days later, multiavidin-dextran conjugate is injected i.v. (in two divided doses, 60 minutes apart). After another 2 days, a dose of multibiotin-dextran-doxorubicin is administered i.v. Five days later, a dose of streptavidin conjugated with doxorubicin is administered i.v.

The preceding examples can be repeated with similar success by substituting the generically or specifically described reactants and/or operating conditions of this invention for those used in the preceding examples.

From the foregoing descriptions, one skilled in the art can easily ascertain the essential characteristics of this invention and, without departing from the spirit and scope thereof, can make various changes and modifications of the invention to adapt it to various usages and conditions.

I claim:

1. An improvement in a method of detecting or treating lesions in a subject, the method comprising the steps of (a) parenterally injecting a subject with a targeting composition comprised of
  (i) a biotin-protein conjugate or
  (ii) an avidin-protein conjugate, wherein the protein of said conjugate binds to a marker substance produced by or associated with the targeted lesion, and allowing said conjugate to accrete at the targeted lesion;

(b) then parenterally injecting a clearing composition comprised of
  (i) avidin, when said targeting composition is a biotin-protein conjugate, or
  (ii) biotin, when said targeting composition is an avidin-protein conjugate, and allowing said clearing composition to substantially clear said targeting composition from non-targeted sites and to bind to said targeting composition accreted at the targeted lesion; and (c) parenterally injecting a detection or therapeutic composition comprised of a conjugate of
  (i) avidin and a detection or therapeutic agent when said clearing composition is biotin, or
  (ii) biotin and a detection or therapeutic agent when said clearing agent is avidin, and allowing said detection or therapeutic composition to accrete at the targeted lesion thereby treating the lesion when said agent is a therapeutic agent, or if said agent is a detection agent, (d) detecting said agent accreted at the lesion, thereby detecting the lesion;

wherein the improvement is that at least one of the compositions of step (a) or (b) further comprises a polymer comprising multiple avidin or biotin binding sites, thereby providing an increased number of binding sites to which a subsequently administered composition of step (b) or (c) binds, thereby amplifying the amount of said detection or therapeutic agent at the targeted lesion.

2. A method of detecting or treating lesions in a subject, the method comprising the steps of (a) injecting the subject with a first composition comprised of
  (1) a multibiotin-polymer-protein conjugate, or
  (2) a biotin-protein conjugate, wherein the protein of said conjugate binds to a marker substance produced by or associated with the target lesion, and allowing said conjugate to accumulate at the target lesion to provide biotin molecules at the lesion;

(b) injecting a clearing agent comprised of
  (1) avidin, or
  (2) a multiavidin-polymer conjugate, or
  (3) a multiavidin-multitherapeutic agent-polymer conjugate or a multiavidin-multidetection agent-polymer conjugate, or
  (4) an avidin-therapeutic agent conjugate or an avidin-detection agent conjugate, or
  (5) a multiavidin-therapeutic agent-polymer conjugate or a multiavidin-detection agent-polymer conjugate, and permitting said clearing agent to remove circulating biotin conjugate;

(c) injecting a localizing agent comprised of
  (1) avidin, or
  (2) a multiavidin-polymer conjugate, or
  (3) a multiavidin-multitherapeutic agent-polymer conjugate or a multiavidin-multidetection agent-polymer conjugate, or
  (4) an avidin-therapeutic agent conjugate or an avidin-detection agent conjugate, or
  (5) a multiavidin-therapeutic agent-polymer conjugate or a multiavidin-detection agent-polymer conjugate, wherein said localizing agent is the same as or different from said clearing agent and is injected concurrently with or subsequent to said clearing agent, and permitting said localizing agent to localize at the target lesion by binding to a biotin molecule;

(d) injecting a composition comprising
  (1) a biotin-therapeutic agent conjugate or a biotin-detection agent conjugate, or
  (2) a polymer-multibiotin conjugate or,
  (3) a polymer-multibiotin-multi-therapeutic agent conjugate or a polymer-multibiotin-multi-detection agent conjugate, and permitting biotin molecules of said composition of step (d) to bind to avidin molecules of said localizing agent of step (c);

(e) if a conjugate containing polymer is used in step (d), then injecting a composition comprising
  (1) an avidin-therapeutic agent conjugate or an avidin-detection agent conjugate, or
  (2) a multiavidin-polymer conjugate, or
  (3) avidin, or
  (4) a multiavidin-multitherapeutic agent-polymer conjugate or a multiavidin-multidetection agent-polymer conjugate, and permitting an avidin molecule of said composition of step (e) to bind to a biotin molecule of said localizing composition of step (d);

(f) if other than said avidin-therapeutic agent conjugate or said avidin-detection agent conjugate has been injected in step (e), injecting a biotin-therapeutic agent conjugate or a biotin-detection agent conjugate and permitting a biotin molecule of said conjugate of step (f) to bind to an avidin molecule at the target lesion thereby treating the lesion when said agent is a therapeutic agent, or if said agent is a detection agent, (g) detecting said agent bound at the lesion, thereby detecting the targeted lesion;

wherein a polymer conjugate is used in at least one step and the polymer has a sufficiently rigid stereochemical structure so that only one avidin or biotin molecule of each conjugate binds to a molecule already present at the target lesion.

3. A method of detecting or treating lesions in a subject comprising the steps of (a) injecting a subject with a first composition comprised of a multiavidin-polymer-protein conjugate or an avidin-protein conjugate, wherein the protein of said conjugate binds to a marker substance produced by or associated with the target lesion, and allowing said conjugate to accrete at the target lesion;

(b) injecting a clearing agent comprised of
  (1) biotin, or
  (2) a multibiotin-polymer conjugate, or
  (3) a multibiotin-multitherapeutic agent-polymer conjugate or a multibiotin-multidetection agent-polymer conjugate, or
  (4) a biotin-therapeutic agent conjugate or a biotin-detection agent conjugate, and permitting said clearing agent to remove circulating conjugate of step (a);

(c) injecting a localizing agent comprised of
  (1) a multibiotin-polymer conjugate, or
  (2) a multibiotin-multitherapeutic agent-polymer conjugate or a multibiotin-multidetection agent-polymer conjugate, or
  (3) a biotin-therapeutic agent conjugate or a biotin-detection agent conjugate, wherein said localizing agent is the same as or different from said clearing agent and is injected concurrently with or subsequent to said clearing agent and permitting said localizing agent to localize at the target lesion by binding to an avidin molecule;

(d) injecting a composition comprised of
  (1) an avidin-therapeutic agent conjugate or an avidin-detection agent conjugate, or
  (2) a polymer-multiavidin conjugate or,
  (3) a polymer-multiavidin-multitherapeutic agent conjugate or a polymer-multiavidin-multidetection agent conjugate, and permitting avidin molecules of said conjugate of step (d) to bind to biotin molecules of said localizing agent;

(e) if a conjugate containing polymer is used in step (d), then injecting a composition consisting essentially of
  (1) a biotin-therapeutic agent conjugate or a biotin-detection agent conjugate, or
  (2) a multibiotin-polymer conjugate, or
  (3) a multibiotin-multitherapeutic agent-polymer conjugate or a multibiotin-multidetection agent-polymer conjugate, and permitting the biotin molecules of the conjugate of step (e) to bind to avidin molecules provided by said composition of step (d);

(f) if other than a biotin-therapeutic agent or a biotin-detection agent has been injected in step (e), injecting an avidin-therapeutic agent conjugate or an avidin-detection agent conjugate and permitting the avidin molecules of the conjugate of step (f) to bind to biotin molecules at the target lesion thereby treating the lesion when said agent is a therapeutic agent, or if said agent is a detection agent;

(g) detecting said agent bound at the lesion, thereby detecting the targeted lesion;

wherein a polymer conjugate is used in at least one step of the method and the polymer has a sufficiently rigid stereochemical structure so that only one biotin or avidin molecule of each conjugate binds to a molecule already present at the target lesion.

4. The method of claim 2 wherein:

said composition of step (a) comprises a multibiotin-polymer-protein conjugate; and provides multiple biotin molecules at the targeted lesion;

said clearing agent of step (b) and said localizing agent of step (c) are comprised of avidin; and said composition of step (d) comprises a biotin-detection agent conjugate or a biotin-therapeutic agent conjugate.

5. The method of claim 2 wherein:

said composition of step (a) is comprised of a biotin-protein conjugate, and provides biotin molecules at the target lesion;

said clearing agent of step (b) and said localizing agent of step (c) are comprised of a multiavidin-polymer conjugate, wherein only one avidin molecule of each multiavidin-polymer conjugate binds to a biotin molecule at the target lesion; and said composition of step (d) comprises a biotin-therapeutic agent conjugate or a biotin-detection agent conjugate.

6. The method of claim 2 wherein:

said composition of step (a) is comprised of a biotin-protein conjugate and provides biotin molecules at the target lesion;

said clearing agent of step (b) and said localizing agent of step (c) are comprised of a multiavidin-polymer-therapeutic agent conjugate or a multiavidin-polymer-detection agent conjugate, wherein only one avidin molecule of each conjugate binds to a biotin molecule present at the target lesion, and said composition of step (d) comprises a biotin-therapeutic agent conjugate or a biotin-detection agent conjugate.

7. The method of claim 3 wherein:

said composition of step (a) is comprised of an avidin-protein conjugate and provides avidin molecules at the target lesion;

said clearing agent of step (b) and said localizing agent of step (c) are comprised of a multibiotin-polymer conjugate, wherein only one biotin molecule of each multibiotin-polymer conjugate binds to an avidin molecule provided by each avidin-protein conjugate accreted at the target lesion, whereby each multibiotin-polymer conjugate provides multiple biotin molecules at the target lesion; and said composition of step (d) comprises an avidin-therapeutic agent conjugate or an avidin-detection agent conjugate.

8. The method of claim 3 wherein:

said composition of step (a) is comprised of an avidin-protein conjugate and provides avidin molecules at the target lesion;

wherein said clearing agent of step (b) and said localizing agent of step (c) are comprised of a multibiotin-polymer-therapeutic agent conjugate or a multibiotin-polymer-detection agent conjugate, wherein only one biotin molecule of each multibiotin-polymer-therapeutic agent conjugate or multibiotin-polymer-detection agent conjugate binds to an avidin molecule provided by each avidin-protein conjugate of step (a) accreted at the target lesion, whereby each multibiotin-polymer-therapeutic agent conjugate or multibiotin-polymer-detection agent conjugate provides multiple biotin molecules and provides a therapeutic agent or detection agent to the target lesion;

and said composition of step (d) comprises an avidin-therapeutic agent conjugate or an avidin-detection agent conjugate.

9. The method of claim 1, wherein the polymer is selected from the group consisting of polyamino-acids, oligonucleotides, polyimines, polysaccharides, polyamines, polycarboxylic acids and polyalcohols.

10. The method of claim 9 wherein the polymer has restricted stereochemistry such that each of the multiple biotin or avidin moieties conjugated to said polymer binds a complementary avidin or biotin moiety subsequently administered, and only one of the said multiple biotin or avidin moieties conjugated to said polymer binds to a complementary avidin or biotin moiety already present at the target site.

11. The method of claim 9, wherein the polymer has a molecular weight of 5,000 to 200,000 kD.

12. The method of claim 1 wherein the polymer is a dextran or a starburst dendrimer.

13. The method of claim 12 wherein the polymer is an aminodextran.

14. The method of claim 1, wherein the lesion is cancerous, cardiovascular, infectious or inflammatory.

15. The method of claim 14, wherein the cardiovascular lesion is a thrombus, embolus, infarct or atherosclerotic plaque.

16. The method of claim 14, wherein the cancerous lesion is a carcinoma, melanoma, sarcoma, neuroblastoma, leukemia, lymphoma, glioma or myeloma.

17. The method of claim 14, wherein the lesion is infectious or inflammatory.

18. The method of claim 1, wherein the protein is selected from the group consisting of a peptide, polypeptide, hormone, lymphokine, growth factor, albumin, cytokine, enzyme, immune modulator, receptor protein, antibody and antibody fragment.

19. The method of claim 18, wherein the protein is one of monoclonal antibody, or a specific binding fragment thereof.

20. The method of claim 19, wherein the fragment is one of a Fv, single chain antibody, Fab, Fab', $F(ab)_2$ or $F(ab')_2$.

21. The method of claim 20, wherein the fragment is one of Fab, Fab', $F(ab)_2$ or $F(ab')_2$.

22. The method of claim 19, wherein the antibody is multispecific.

23. The method of claim 22, wherein the antibody is multispecific to differing epitopes or molecules of a marker substance.

24. The method of claim 18, wherein the protein has a specific immunoreactivity to a marker substance of at least 60% and a cross-reactivity to other antigens or non-target substances of less than 35%.

25. The method of claim 1, wherein the method is for detection of a lesion.

26. The method of claim 25, wherein the method comprises one of external imaging of said patient or internal detection of said patient.

27. The method of claim 26, wherein said internal detection is effected during an operative, intravascular or endoscopic procedure.

28. The method of claim 25, wherein the detection agent is one of a radionuclide, mri enhancing agent, photoactivated dye or differentiation agent.

29. The method of claim 25, wherein the detection agent is one of a gamma-emitter, positron-emitter, x-ray-emitter, beta-emitter or fluorescence-emitter.

30. The method of claim 28, wherein the detection agent is a radionuclide with an energy between 10 and 7000 keV.

31. The method of claim 29, wherein the radionuclide used for external imaging is one of Iodine-123, Iodine-131, Indium-111, Gallium-67, Ruthenium-97, Technetium- 99m, Cobalt-57, Cobalt-58, Chromium-51, Iron-59, Selenium-75, Thallium-201, or Ytterbium-169.

32. The method of claim 29, wherein the radionuclide used for internal detection is Iodine-125, Iodine-123, Iodine-131, Indium-111, Technetium-99m or Gallium-67.

33. The method of claim 28, wherein the mri enhancing agent is a species of one of Gadolinium, Iron, Manganese, Rhenium, Europium, Lanthanium, Holmium, or Terbium.

34. The method of claim 1, wherein the method is for treating a lesion.

35. The method of claim 34, wherein the therapeutic agent is one of an isotope, drug, toxin, fluorescent dye activated by nonionizing radiation, hormone, hormone antagonist, receptor antagonist, enzyme or proenzyme.

36. The method of claim 35, wherein the therapeutic agent is an electron- or neutron-capturing agent.

37. The method of claim 35, wherein the therapeutic agent is an isotope which is one of Iodine-125, Iodine-131, Actinium-225, Bismuth-212, Bismuth- 213, Lead-212, Rhenium-186, Rhenium-188, Silver-111, Platinum- 197, Palladium- 109, Copper-67, Phosphorus-32, Phosphorus-33, Yttrium-90, Scandium-47, Samarium-153, Lutetium-177, Rhodium- 105, Praseodymium-142, Praseodymium-143, Terbium-161, Holmium-166, or Gold-199.

38. The method of claim 34, wherein the therapeutic agent is an anti-DNA, anti-RNA, radiolabeled oligonucleotide, anti-protein or anti-chromatin cytoxic or antimicrobial agent.

39. The method of claim 36, wherein the therapeutic agent is a drug which is one of taxol, mechlorethamine, cyclophosphamide, melphalan, uracil mustard, chlorambucil, thiotepa, busulfan, carmustine, lomustine, semustine, streptozocin, dacarbazine, methotrexate, fluorouracil, cytarabine, azaribine, mercaptopurine, thioguanine, vinblastine, vincristine, dactinomycin, daunorubicin, doxorubicin, bleomycin, mithramycin, mitomycin, L-asparaginase, cisplatin, hydroxyurea, procarbazine, mitotane, prednisone, hydroxyprogesterone caproate, medroprogesterone acetate, diethylstilbestrol, ethinyl estradiol, tamoxifen, and testosterone propionate or fluoxymesterone.

40. The method of claim 35, wherein the therapeutic agent is a toxin which is one of abrin, alpha toxin, diphtheria toxin, exotoxin, gelonin, pokeweed antiviral protein, ricin, or saporin.

41. A sterile injectable composition for human use comprising a detection or therapeutic composition comprised of (i) a multiavidin-polymer-protein conjugate, (ii) a multiavidin-polymer conjugate, (iii) a multiavidin-polymer-detection agent conjugate or multiavidin-polymer-therapeutic agent conjugate, (iv) a multibiotin-polymer conjugate (v) a multibiotin-polymer-protein conjugate or (vi) a multibiotin-polymer-therapeutic agent conjugate or a multibiotin-polymer detection agent conjugate, wherein the protein of said conjugate preferentially binds to a marker substance produced by or associated with a targeted lesion and wherein the polymer of said conjugate has a sufficiently rigid stereochemical structure so that one avidin or biotin molecule of the conjugate binds to one biotin or avidin molecule already present at the target lesion.

42. The method of claim 2, wherein the clearing agent of step (b) and the localizing agent of step (c) are the same, and wherein steps (b) and (c) are effected together by one injection.

43. The method of claim 3, wherein the clearing agent of step (b) and the localizing agent of step (c) are the same, and wherein steps (b) and (c) are effected together by one injection.

* * * * *